United States Patent
Crespin et al.

(10) Patent No.: US 11,730,415 B2
(45) Date of Patent: Aug. 22, 2023

(54) METHOD AND SYSTEM FOR ANALYZING HEART RHYTHMS

(71) Applicant: IMPLICITY, Montrouge (FR)

(72) Inventors: Eliot Crespin, Joinville-le-Pont (FR); Arnaud Rosier, Montrouge (FR); David Perlmutter, Paris (FR)

(73) Assignee: IMPLICITY, Montrouge (FR)

( * ) Notice: Subject to any disclaimer, the term of this patent is extended or adjusted under 35 U.S.C. 154(b) by 275 days.

(21) Appl. No.: 17/172,423

(22) Filed: Feb. 10, 2021

(65) Prior Publication Data

US 2021/0386354 A1     Dec. 16, 2021

Related U.S. Application Data

(60) Provisional application No. 63/037,081, filed on Jun. 10, 2020.

(51) Int. Cl.
| | |
|---|---|
| *A61B 5/00* | (2006.01) |
| *A61B 5/352* | (2021.01) |
| *A61B 5/366* | (2021.01) |
| *A61B 5/363* | (2021.01) |
| *A61B 5/361* | (2021.01) |

(52) U.S. Cl.
CPC ............ *A61B 5/352* (2021.01); *A61B 5/0006* (2013.01); *A61B 5/361* (2021.01); *A61B 5/363* (2021.01); *A61B 5/366* (2021.01); *A61B 5/7267* (2013.01)

(58) Field of Classification Search
CPC ....... A61B 5/352; A61B 5/0006; A61B 5/361; A61B 5/363; A61B 5/366; A61B 5/7267; A61B 5/7264
See application file for complete search history.

(56) References Cited

U.S. PATENT DOCUMENTS

| | | |
|---|---|---|
| 2013/0253355 A1 | 9/2013 | Fahey |
| 2019/0167143 A1 | 6/2019 | Li et al. |

OTHER PUBLICATIONS

Yan et al. "Fusing Transformer Model with Temporal Features for ECG Heartbeat Classification." 2019 IEEE International Conference on Bioinformatics and Biomedicine (BIBM). IEEE, 2019. pp. 898-905.

Bitarafan et al. "A Hybrid Deep Model for Automatic Arrhythmia Classification based on LSTM Recurrent Networks." 2020 IEEE International Symposium on Medical Measurements and Applications (MeMeA). IEEE, 2020. 6 pages.

Chen et al. "Automated arrhythmia classification based on a combination network of CNN and LSTM." Biomedical Signal Processing and Control. 57 (2020): 101819. 10 pages.

(Continued)

*Primary Examiner* — Scott M. Getzow
(74) *Attorney, Agent, or Firm* — Maier & Maier, PLLC

(57) ABSTRACT

A method and a system for analyzing electrocardiographic segments previously derived from a cardiac device so as to help to discriminate true positives episodes, including abnormal heart rhythms, from false positives episodes, including normal heart rhythms. Each episode received includes at least one segment of electrocardiographic signal, and each segment is segmented into sub-segments. Score vectors are obtained for each sub-segment to classify the episode so as to discriminate true positive episodes from false positive episodes, and the classification results, which include at least the true positive episodes, are output.

20 Claims, 2 Drawing Sheets

(56) References Cited

OTHER PUBLICATIONS

Mousavi et al. "Single-modal and multi-modal False Arrhythmia Alarm Reduction using Attention-based Convolutional and Recurrent Neural Networks." PloS one 15.1 (2020): e0226990. 9 pages.
Meyer et al. "Combining Algorithms in Automatic Detection of QRS Complexes in ECG Signals." IEEE Transactions on Information Technology in Biomedicine 10.3 (2006): 468-475.

METHOD AND SYSTEM FOR ANALYZING HEART RHYTHMS

FIELD

The present invention pertains to the field of electrophysiological signal analysis. In particular, the invention relates to a system and a method for analyzing electrocardiographic episodes acquired from a cardiac monitoring device so as to discriminate true positives episodes, comprising abnormal heart rhythms, from false positives episodes, comprising normal heart rhythms.

BACKGROUND

An electrocardiogram (ECG or EKG) records the electrical signals from the heart. The waves of an ECG signal and referred to by letter.

An insertable or implantable cardiac monitor is a small heart-monitoring device that continuously measures ECG signal for a long-term time period (e.g., up to several years). Some of those insertable or implantable cardiac monitors are further configured to continuously analyze the measured ECG signal and identify abnormal heart rhythm, also called episodes, and records only said episodes. Insertable or implantable cardiac monitors wirelessly transmit the recorded episodes (i.e., segments of the measured ECG signal) to an Internet-connected transmitter or other connected devices such as a mobile phone, which transmits the ECG signals to a healthcare professional via the Internet. Those healthcare professionals can then view or print the ECG signals using a software platform to identify cardiac episodes by making subjective determinations based on their training and experience. In addition to automatic episodes transmissions, insertable or implantable cardiac monitors are programmed to transmit an alert (along with the potentially abnormal ECG signal) to the healthcare professionals.

Conventional platforms for viewing ECG signals received from insertable or implantable cardiac monitors have a number of drawbacks. First, insertable or implantable cardiac monitors are sensitive and designed to output an alert in response to all abnormal rhythmic episodes. As a result, insertable or implantable cardiac monitors output a significant number of false positive alerts. Requiring physicians to review and evaluate false positive alerts places unnecessary strain on physicians, adds costs to the health care system, and can cause added stress for the individual patient being monitored.

Secondly, the insertable or implantable cardiac monitors from the leading manufacturers all output data to their own device-specific platform. Therefore, healthcare professionals treating patients with insertable or implantable cardiac monitors from different manufacturers must learn and use a number of different platforms.

Finally, conventional platforms are not configured to allow software analysis of ECG signals. Instead, conventional platforms generally output information to electronic medical records systems and reports for a physician to view and evaluate. Physicians are then expected to make a subjective determination based on their training and experience.

SUMMARY

This invention thus relates to computer-implemented method for analyzing electrocardiographic episodes previously derived from a cardiac connected device so as to discriminate true positives episodes, comprising abnormal heart rhythms, from false positives episodes, comprising normal heart rhythms; said method comprising:
  receiving the episodes, each episode comprising at least one segment of electrocardiographic signal;
  for each segment in one episode:
    identifying R waves in the segment using at least one algorithm and using said R waves for calculating at least one feature of the segment;
    segmenting the segment into at least one sub-segment or at least two overlapping sub-segments;
    for each sub-segment:
      using the R waves identified in said sub-segment for calculating at least one feature of the sub-segment;
      providing as input to a machine learning algorithm the at least one feature of the sub-segment and the at least one feature of the segment and obtaining as output a score vector, the machine learning algorithm being configured to output said score vector;
    using the score vectors obtained for each sub-segment in one episode to classify the episode so as to discriminate true positives episodes from false positives episodes;
    outputting the true positives episodes.

Advantageously, the present method allows to reduce the number of false positive episodes to be reviewed by the medical staff. Indeed, the combination of global information on the episode, obtained as the feature(s) of the segment(s) with more local information, obtained as the feature(s) of the sub-segment(s) improves the efficiency of rejections of the false positive episodes.

The method may output for all analyzed episodes their class: true positive or false positive. Furthermore, the machine learning algorithm may be configured to classify the abnormal cardiac rhythms into different classes associated to specific pathologies. Information on the class of abnormal cardiac rhythms may be then provided for each sub-segment into the score vector and used to determine, for the true positive episodes, which is the abnormal cardiac rhythms that is present in it. This provides further useful information to the users.

According to one embodiment, the method comprises providing the true positive episodes to a remote monitoring platform, so as to increase the information available on the remote monitoring platform itself and, eventually, make available the output of the method to the medical staff thorough the platform.

According to one embodiment, for each segment in one episode the at least one feature of the segment that is calculated is at least one of the following: morphological feature and/or rhythm feature. The morphological features are advantageously extracted for the segments since they provide an analysis of the morphology of P waves and the QRS complex along the whole segment, and are able to capture irregularities which are characteristic of long episodes (such as AT/AF and ventricular tachycardia, most notably).

The rhythm features are advantageously extracted for the segment since they provide an analysis of the R-peaks statistically, and capture the pattern of R-peaks intervals. Such patterns can be highly useful to differentiate between long abnormalities (AT/AF or normal Rhythm with premature ventricular contractions/premature atrial contractions).

According to one embodiment, for each sub-segment the feature of the sub-segment to be calculated is at least one of the following: rhythm feature, variation feature, neural network features and/or spectral feature. Advantageously the variation features are extracted only for the sub-segment since the analysis of the variation of the signal over various time frame allows quantifies the amount of signal which can be explained by cardiac origins or non-cardiac origins (artifact). The spectral features obtained for the sub-segment are particularly advantageous because the results from an analysis of the frequency of the cardiac signal, characterizing the regularity of the signal, and can differentiate between low frequency regular signals (normal rhythm), low frequency irregular signals (various abnormalities), and high frequency signals (artifact).

The present invention also relates to a system for analyzing electrocardiographic episodes previously derived from a cardiac device so as to discriminate true positives episodes, comprising abnormal heart rhythms, from false positives episodes, comprising normal heart rhythms, said system comprising:

at least one input adapted to receive the episodes, each episode comprising at least one segment of electrocardiographic signal;
at least one processor configured to:
for each segment in one episode:
identifying R waves in the segment using at least one algorithm and using said R waves for calculating at least one feature of the segment;
segmenting the segment into at least two overlapping sub-segments;
for each sub-segment:
using the R waves identified being comprised in the sub-segment for calculating at least one feature of the sub-segment;
providing as input to a machine learning algorithm the at least one feature of the sub-segment and the at least one feature of the segment, wherein the machine learning algorithm is configured to output a score vector;
using the score vectors obtained for each sub-segment in one episode to classify the episode so as to discriminate true positives episodes from false positives episodes;
at least one output adapted to provide the true positives episodes.

According to one embodiment, for each segment in one episode the at least one feature of the segment is at least one of the following: morphological feature and/or rhythm feature.

According to one embodiment, for each sub-segment the calculated feature of the sub-segment is at least one of the following: rhythm feature, variation feature and/or spectral feature.

According to one embodiment, the morphological features are statistics calculated based on the shape of the ECG signal and the rhythm features are statistics calculated based on time periods between R waves. These statistics may be directly calculated on specific functions (ex minimum, maximum, median, standard deviation or more complex functions). However, here statistic refers as well to some categorical features (ex: type of p-wave, which can be positive, negative or unknown) which are computed from the previous statistics.

According to one embodiment, the processor is further configured to input each sub-segment of the episode into a neural network and extract as output of the neural network at least one neural network feature of the sub-segment. Said neural network feature being one of the features of the sub-segment provided as input to the machine learning algorithm. In this embodiment, for each sub-segment the calculated feature of the sub-segment is at least one of the following: rhythm feature, variation feature, neural network features and/or spectral feature.

According to one embodiment, the neural network is a convolutional neural network.

According to one embodiment, the at least one algorithm for identifying R waves is selected from the following list: XQRS detection algorithm, a stationary wavelet transform process and/or an optimized knowledge based (OKB) detection algorithm.

According to one embodiment, the processor is configured to identifying R waves in the segment using the at least two algorithms and use a combining algorithm configured to combine the R waves obtained from the at least two algorithms, so as to obtained corrected R waves.

According to one embodiment, the R waves in the episodes are identified using at least two algorithms and the at least one rhythm feature of the segment and sub-segment is calculated using the R waves obtained from each of the at least two algorithms. Notably, the at least one rhythm feature of the segment and sub-segment is calculated using the corrected R waves obtained from the combining algorithm. This embodiment advantageously allows to reduce the error on the estimation on the position of the R waves and therefore obtain a more accurate evaluation of the segments and sub-segments features.

According to one embodiment, the machine learning algorithm is trained on a dataset comprising a plurality of annotated episodes, wherein the dataset comprises episodes representative of abnormal heart rhythms.

According to one embodiment, the dataset of annotated episodes comprises episodes associated to an asystole, bradycardia, atrial fibrillation, atrial tachycardia, ventricular tachycardia, other abnormalities and/or an artifact.

According to one embodiment, the machine learning algorithm is an XGBoost algorithm.

According to one embodiment, the input is further configured to receive episodes from a plurality of cardiac devices from a plurality of manufacturers.

According to one embodiment, the processor is further configured to normalize the episodes received from the plurality of cardiac devices.

The present invention further relates to a non-transitory computer readable storage medium comprising instructions which, when the program is executed by a computer, cause the computer to carry out the steps of the method.

The present invention concerns a computer implemented method for identifying abnormal heart rhythms, the method comprising:

receiving an electrocardiogram (ECG) signal from a cardiac device, the ECG signal including a series of R waves;
identifying the R waves in the ECG signal;
calculating morphological features of the ECG signal;
calculating rhythm features of the ECG signal;
segmenting the ECG signal into a series of overlapping segments;
calculating variation features of each segment;
calculating rhythm features of each segment;
calculating spectral features of each segment;
training a machine learning algorithm on a dataset of annotated ECG segments that includes ECG segments indicative of abnormal heart rhythms;
classifying each segment, by the machine algorithm, based on the variation features of the segment, the rhythm features of the segment, the spectral features of the segment, the morphological features of the ECG signal, and the rhythm features of the ECG signal; and classifying the ECG signal based on the classifications of the segments.

According to one embodiment, the morphological features of the ECG signal are statistics calculated based on the shape of the ECG signal.

According to one embodiment, the rhythm features are statistics calculated based on time periods between waves.

According to one embodiment, the R waves in the ECG signal are identified using a plurality of methods, the rhythm features of the ECG signal are calculated for each of the plurality of methods, and the rhythm features of each segment are identified for each of the plurality of methods.

According to one embodiment, the plurality of methods includes an XQRS detection method, a stationary wavelet transform process, or an optimized knowledge based (OKB) detection method.

According to one embodiment, the dataset of annotated ECG segments includes ECG segments indicative of an asystole, bradycardia, atrial fibrillation or atrial tachycardia, ventricular tachycardia or ventricular fibrillation, or an artifact.

According to one embodiment, the machine learning algorithm is an XGBoost algorithm.

According to one embodiment, the method further comprises receiving ECG signals from a plurality of cardiac devices from a plurality of manufacturers.

According to one embodiment, the method further comprises normalizing the ECG signals received from the plurality of cardiac devices.

According to one embodiment, the method further comprises providing a platform to view the received ECG signal and the classification of the received ECG signal.

In the present invention, the following terms have the following meanings:

"Episode": refers to a portion of electrocardiographic signal having finite time duration which have been identified and recorded by the manufacturer of the cardiac device used to measure the electrocardiographic signal itself. Indeed, manufacturers may implement an identification method configured to perform a preliminary analysis on the measured electrocardiographic signal so as to identify in the measured signal a portion of electrocardiographic signal associated to a cardiac abnormal rhythm and then record it. The portion of electrocardiographic signal may be as well recorded if a patient triggers the recording. The episode comprises further to a portion of electrocardiographic signal also a date of the recording (day and time) and the type of recording (i.e., patient or identification method or triggered episode). The episodes recorded from a cardiac device depends intrinsically from the cardiac device itself (i.e., quality of signal acquired) and the identification method of the manufacturers (i.e., accuracy of the discrimination) and therefore may be different between devices of one manufacturer and between different devices of different manufacturers.

"Cardiac (connected) device" refers to devices configured to measure electrocardiographic signal and perform at least one preliminary analysis of the ECG signal in order to detected episodes according to an identification method, and transfer said episodes to an external receiver. Said devices may be for example implantable loop recorder, mobile cardiac telemetry, insertable cardiac monitor and the like.

"Abnormal heart rhythms" refers to any physiological abnormality which can be identifiable on the cardiac signal. For instance, within the present invention, the following abnormalities may be identified but not limited to: "Sinoatrial block, paralysis or arrest", "Atrial Fibrillation", "Atrial fibrillation or flutter", "Atrial Flutter", "Atrial tachycardia", "Junctional tachycardia", "Supraventricular tachycardia", "Sinus tachycardia", "Ventricular tachycardia", "Pacemaker", "Premature ventricular complex", "Premature atrial complex", "First degree atrio-ventricular block (AVB)", "$2^{nd}$ degree AVB Mobitz I", "$2^{nd}$ degree AVB Mobitz II", "$3^{rd}$ degree AVB", "Wolff-Parkinson-White syndrome", "Left bundle branch block", "Right bundle branch block", "Intraventricular conduction delay", "Left ventricular hypertrophy", "Right ventricular hypertrophy", "Acute myocardial infarction", "Old myocardial infarction", "Ischemia", "Hyperkalemia", "Hypokalemia", "Brugada", "Long QTc", etc. . . .

The term "processor" should not be construed to be restricted to hardware capable of executing software, and refers in a general way to a processing device, which can for example include a computer, a microprocessor, an integrated circuit, or a programmable logic device (PLD). The processor may also encompass one or more Graphics Processing Units (GPU), whether exploited for computer graphics and image processing or other functions. Additionally, the instructions and/or data enabling to perform associated and/or resulting functionalities may be stored on any processor-readable medium such as, e.g., an integrated circuit, a hard disk, a CD (Compact Disc), an optical disc such as a DVD (Digital Versatile Disc), a RAM (Random-Access Memory) or a ROM (Read-Only Memory). Instructions may be notably stored in hardware, software, firmware or in any combination thereof.

"Machine learning algorithm (ML)" designates in a traditional way computer algorithms improving automatically through experience, on the ground of training data enabling to adjust parameters of computer models through gap reductions between expected outputs extracted from the training data and evaluated outputs computed by the computer models.

"Datasets" refers to collections of data used to build an ML mathematical model, so as to make data-driven predictions or decisions. In supervised learning (i.e. inferring functions from known input-output examples in the form of labelled training data), three types of ML datasets (also designated as ML sets) are typically dedicated to three respective kinds of tasks: training, i.e. fitting the parameters, validation, i.e. tuning ML hyperparameters (which are parameters used to control the learning process), and testing, i.e. checking independently of a training dataset exploited for building a mathematical model that the latter model provides satisfying results.

"Neural network or artificial neural network (ANN)" refers to a category of ML comprising nodes (called neurons), and connections between neurons modeled by weights. For each neuron, an output is given in function of an input or a set of inputs by an activation function. Neurons are generally organized into multiple layers, so that neurons of one layer connect only to neurons of the immediately preceding and immediately following layers.

"QRS" or "QRS complex" refers to the deflections in an electrocardiogram tracing that represent the ventricular activity of the heart. The QRS complex generally comprises the Q wave, the R wave and the S wave which occur in rapid succession.

"False positive" refers to is an error in binary classification in which a test result incorrectly indicates the presence of a condition such as an abnormal rhythm in one episode when the abnormal rhythm is not present, while a "false negative" is the opposite error where the test result incorrectly fails to indicate the presence of a condition when it is present. These are the two kinds of errors in a binary test, in contrast to the two kinds of correct result, a "true positive" and a "true negative".

"Remote monitoring platform" refers to any system for data management configured to receive and store and/or analyze data received from at least one cardiac device corresponding to at least one patient. In one example, said platform may, in general, receive data from one or more cardiac devices of patients to manage the care of those patients, including receipt of data, reports, and information from such devices to enable a healthcare personal to view, document, report on the health status of the patients. Such data may be received at the remote monitoring platform through many sources, including the corresponding device, a device programming machine, reporting from the patient or a manufacturer, or from a third-party entity receiving the data from the device. In this example, the remote monitoring platform may also provide one or more interfaces through which healthcare personal or other users of the platform may manage the receipt of the device data.

BRIEF DESCRIPTION OF THE DRAWINGS

Features and advantages of the invention will become apparent from the following description of embodiments of a system, this description being given merely by way of example and with reference to the appended drawings in which.

DETAILED DESCRIPTION

Figure 1:
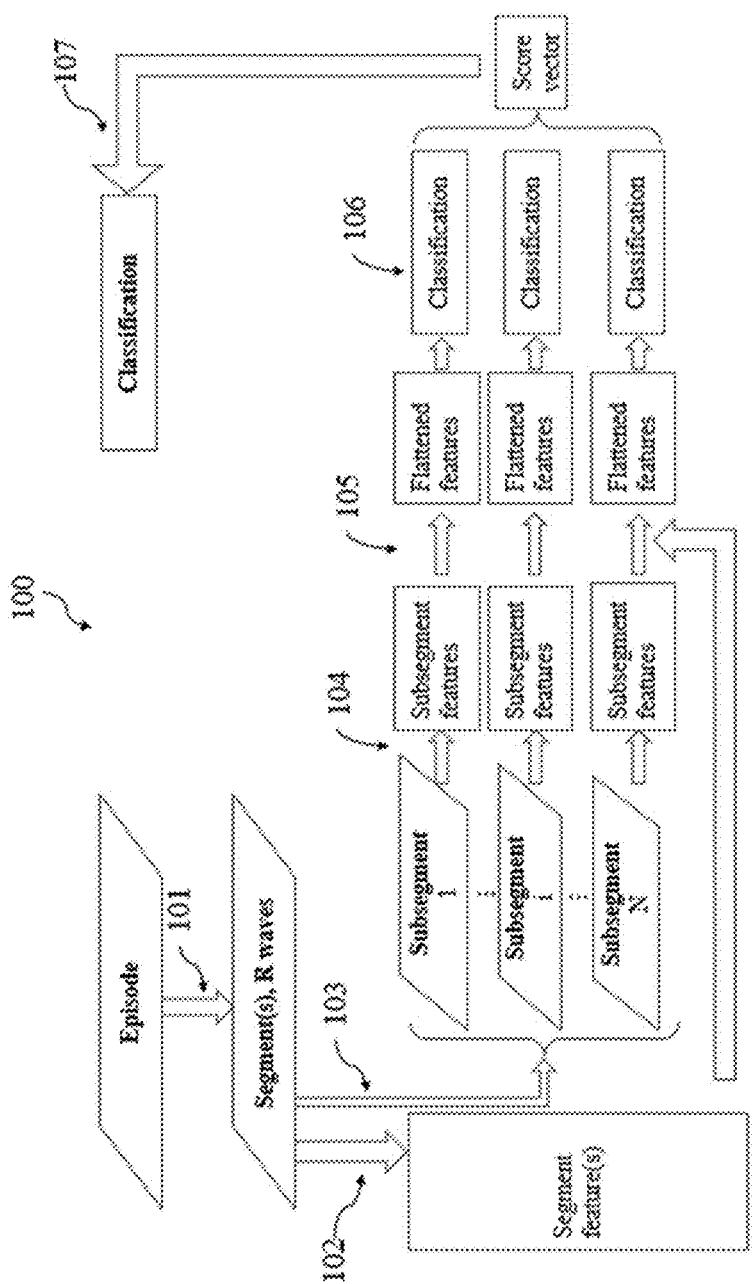
FIG. 1 is a flow chart showing the main steps of the present method according to one embodiment.
Figure 2:
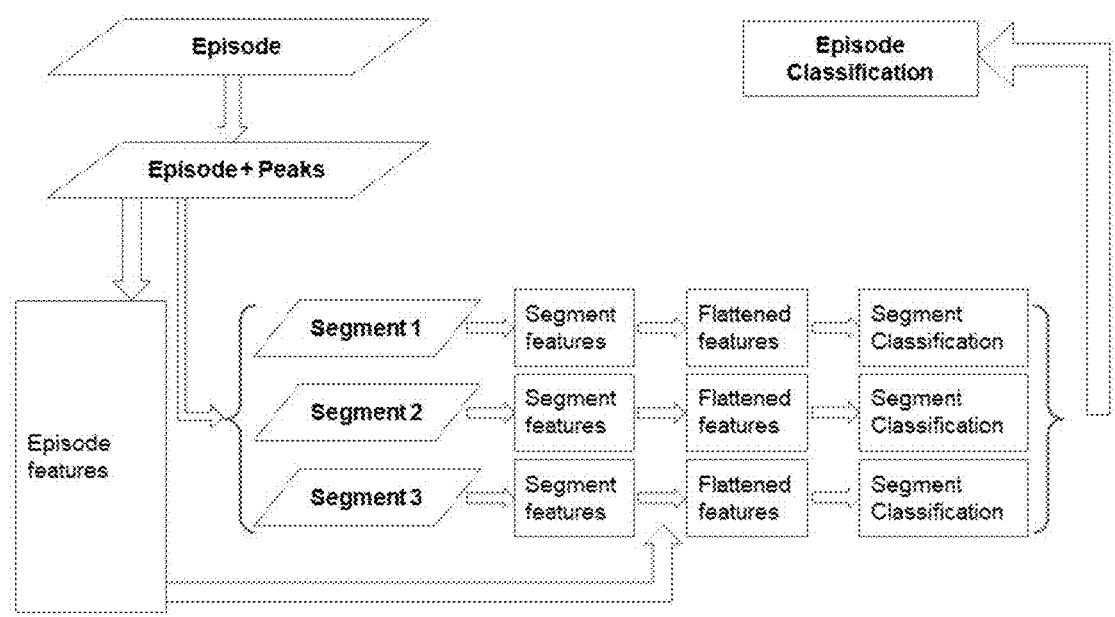
FIG. 2 is a flow chart showing the main steps of the present method according to one embodiment.

The following detailed description will be better understood when read in conjunction with the drawings. For the purpose of illustrating, the computer implemented method and system for analyzing electrocardiographic episodes are shown in the preferred embodiments. It should be understood, however that the present invention is not limited to the precise arrangements, structures, features, embodiments, and aspect shown. The drawings are not drawn to scale and are not intended to limit the scope of the claims to the embodiments depicted. Accordingly, it should be understood that where features mentioned in the appended claims are followed by reference signs, such signs are included solely for the purpose of enhancing the intelligibility of the claims and are in no way limiting on the scope of the claims.

In order to overcome those and other drawbacks of conventional heart monitoring platforms, there is provided a device-diagnostic platform that receives and normalizes ECG signals from any cardiac device (e.g., implantable loop recorder, pacemaker, defibrillator, etc.) produced by any manufacturer. Accordingly, a single platform is provided for healthcare professionals to monitor all of their patients with cardiac implants.

The portion of electrocardiographic signal being the episode may be one segment of a few seconds up to 15 minutes when the observed anomaly in the heart rhythms is of short duration (for example when the criteria for detecting the anomaly is only valid at one single point). However, some of the observed anomalies may have a relatively long duration and do not present any significant variation during their appearance. In these cases, the cardiac device that identifies one of these abnormal heart rhythms may be configured to record as episode a first segment of ECG corresponding to be beginning of the abnormal heart rhythm and a second segment of ECG covering the end of the abnormal heart rhythm. The recording of the whole episode should take too much memory space. According to the manufacture design, a cardiac device may as well record more than two segments for one episode.

The disclosed computer-implemented method and system also include a machine learning algorithm that reviews episodes received from cardiac devices and identifies true abnormal heart rhythms and true normal heart rhythms thereby eliminating the need for a physician to manually review false positive alerts output by cardiac device. The machine learning algorithm uses a rule-based process to review episodes received from cardiac devices, a process that previously required physicians to subjectively review a significant number of episodes. An exemplary method of identifying abnormal heart rhythms, so as to discriminate true positives episodes, comprising abnormal heart rhythms, from false positives episodes, comprising normal heart rhythms, is described below.

The episodes recorded from a cardiac device, for example an insertable or implantable cardiac monitor, are received. Said recorded episode may have been previously transmitted from the cardiac device to a receiving device configured to store the episode in a medical database. The method can therefore receive said episodes stored in the medical database.

The ECG segments received from the cardiac devices (referred to herein as "episodes") are generally between approximatively 9 seconds and approximatively 5 minutes in length.

As shown in FIG. 1, the method 100 comprises a first step 101 wherein the R waves are identified in each segment of one episode. According to one embodiment, the R waves in the segment are identified using at least one algorithm. The at least one algorithm for identifying R waves may be selected from the following list: a XQRS detection algorithm, a stationary wavelet transform process and/or an optimized knowledge based (OKB) detection algorithm.

In the XQRS detection algorithm, the ECG segment is bandpass filtered between 5 and 20 Hz to get a filtered ECG segment. A moving wave integration (MWI) with a ricker wavelet is applied onto the filtered ECG segment and the square of the integrated signal is saved. Calibration is conducted to initialize running parameters of noise and QRS amplitudes, a QRS detection threshold, and recent RR intervals. If calibration fails, default parameters are used. For each local maxima of the MWI signal, the XQRS detection method determines whether the local maxima is a QRS complex. To be classified as a QRS, it must come after the refractory period, cross the QRS detection threshold, and not be classified as a T-wave if it comes close enough to the previous QRS. If successfully classified, the running detection threshold and heart rate parameters are updated. If not classified as a QRS, the local maxima is classified it as a noise peak and the running parameters are updated. The local maxima of the QRS complex corresponds to the position of the peak of the R wave in the QRS complex (i.e., R peak). For each new QRS detected, the RR interval list is computed, by calculating the time difference between each consecutive R-peak. Upon reaching a new local maxima, the XQRS computes the duration between this local maxima and the last identified R-peak. If this duration is inferior to 1.66 times the most recent RR interval (calculated as the duration between the last identified R-peak, and the one before), the classification of this local maxima as a QRS or not is performed. If no QRS was detected within 1.66 times the recent RR interval. If not, a back-search QRS detection is performed on the previous peaks using a lower QRS detection threshold, before classifying the local maxima.

In the stationary wavelet transform process, the order 2 wavelet transform of the ECG segment is computed, a threshold is applied to the 2nd level detail coefficients of the wavelet transform based on its average and standard deviation, the process is iterated over the thresholded coefficient with windows of constant length with no overlapping. One QRS complex is placed on the maximum coefficients for each window where the thresholded coefficient is not a constant zero, every QRS complex that is within the maximum allowed RR interval range is merged, and the position of each QRS complex is corrected to place it on a local maximum of the ECG segment before computation of the order 2 wavelet transform. As for the previous algorithm, knowing the correct position of the QRS complex allows to determine the position of the corresponding R peak.

In the OKB detection method, the ECG segment is bandpass filtered using a 3rd order Butter bandpass filter, the filtered signal is squared, a QRS moving average and a beat moving average of the squared signal is computed (with windows of respectively the length of a QRS and the length of a beat), blocks of interest are generated using the beat moving average to threshold the QRS moving average, and, for each block of interest, a QRS complex is placed on the local maximum of the original ECG segment on said block. As for the previous algorithms, knowing the correct position of the QRS complex allows to determine the position of the corresponding R peak.

The R peaks obtained from each of the three algorithms may be used to calculate the RR intervals in each ECG segment.

According to one embodiment, the R waves in the episodes are identified using at least two of algorithms listed above.

Alternatively, the R waves may be identified using a novel combining algorithm developed by the inventors that employs the XQRS detection algorithm, the stationary wavelet transform process, and the optimized knowledge based (OKB) detection algorithm.

In this embodiment, the R peaks identified by the three methods above are repositioned on local extrema. The R peaks detected in at least 2 of the 3 algorithm are used for this embodiment. A list of long RR intervals that are at least x times longer than the median RR interval is created (where x is an empirically determined float). A position of supposed supplementary R peaks is inferred (by putting them at the median RR distance from the previous R peak) for each of those long RR intervals in the list. Ratios between the mean gradient (respectively amplitude) in these supposed R peak zone and the mean gradient (respectively amplitude) of the surrounding areas are computed for each new supposed R peak. The R peaks with ratios that are larger than an empirically defined threshold are kept. These last 4 steps are repeated with an adaptive median interval (based on a moving median of the RR intervals). On each iteration, the current result is recombined with the previous one. Then, the median RR interval is computed based on the new R peaks locations (old estimation plus new estimation) and the process is repeated. This iteration improves the detection of RR peaks in the case where gaps multiple R peaks were missed by the previous methods. The repetition is performed until it stops adding new R peaks. Advantageously, this embodiment allows a more accurate repositioning of the R peaks which improves the discrimination ability of present method.

The position of the peaks of the R waves may be used for calculating at least one feature of each segment of one episode (step 102 of the method).

According to one embodiment, for each segment of each episode, at least one morphological feature and/or at least one rhythm feature are calculated. The morphological features may be statistics calculated based on the shape of the ECG signal. The rhythm features may be statistics calculated based on time periods between waves (e.g., time periods between each R peak). Clustering is one example of rhythm feature.

The morphological features may include QRS features and P-wave features. To determine QRS features, a QRS rhythm is extracted for each R peak (based on 2 predefined delays, the one before the R peak and the one after), the median QRS rhythm is computed, each QRS rhythm is assigned its mean and maximum distance to the median QRS, QRS rhythms having mean and maximum distances smaller than predefined thresholds are selected, the beginning and the end of the QRS peak is defined (based on a local extrema analysis) for each of those representative QRS rhythms, and the following features are identified: the median of the QRS peak widths, the median of the QR delays, the median of the RS delays, the median of the QR delays, the standard deviation of the QS delays, and the maximal value of the QS delays.

To determine the P-wave features, R peaks that define the most representative QRS complexes are identified, a rhythm which is approximately a PR rhythm is extracted (based on 2 delays from the R peak) for each R peak, the median signal of all the PR rhythms is computed, the P wave (which is assumed to be the peak with maximal amplitude) is located on the median signal, the prominence and the area of that wave is identified, and the mean distance between the median signal and all the PR rhythms are identified. The P wave (which is assumed to be the peak with maximal amplitude) is also located on all of the PR rhythms and the standard deviation of the PR delays are identified.

The rhythm features may be calculated for each segment using the R peaks detected with each of the four rhythm extraction algorithms described above (the XQRS detection algorithm, the stationary wavelet transform process, the OKB detection algorithm, and the combining algorithm developed by the inventors). The following features may be calculated for each group of R peaks detected in each segment for each algorithm: the mean, median, minimum, maximum and standard deviation of the RR interval durations; the mean, median and standard deviation of the absolute variation of the RR interval durations; and the sample entropy of the RR interval durations, using vectors of length 2, and the Chebyshev distance.

For each of the four rhythm extraction algorithms, the R peak locations array may be transformed into a 3 dimensions vector. The first dimension is the RR intervals from the first R peak to the second-to-last R peak, the second dimension is the RR intervals from the second R peak to the last R peak, and the third dimension is the first peak position to the third-to-last R peak position, adjusted by norm factors. These 3 dimension vectors are grouped into clusters by a clustering algorithm such as the DBScan algorithm. For said clustering, different algorithm may be used such as for example: DBScan, K-Means, MeanShift, Spectral Clustering, Birch or Ward. The clusters are grouped between regular clusters, for which the first two dimensions are close (i.e., the RR intervals at time n and n−1 are close), and irregular clusters for which they are distant. Based on the RR intervals and the clustering, multiple statistics are calculated, comprising: the number of identified clusters, a score of the clustering, the proportion of unclassified rhythms (that did not fall in any cluster) over all rhythms, the proportion of rhythms in regular clusters over all rhythms, the standard deviation of rhythm variations in regular clusters, the average and standard deviation of the difference between the first two dimensions of rhythms in regular clusters, the ratio between the average period of the fastest cluster and the slowest cluster, and the time overlap between these clusters.

In one embodiment, in addition to the at least one rhythm feature, variation feature and/or spectral feature, at least one neural network feature is calculated for each sub-segment of each episode. Each sub-segment of the episode may be provided as input to a neural network so as to extract as output of the neural network at least one neural network feature. Advantageously the neural network is used to identify in the patterns in signals which are undocumented in the literature.

Said neural network may be a convolutional neural network. A convolutional neural network is a type of neural network which takes advantages of the continuity of the ECG data. The convolutional neural network may be trained and validated on a subset the XGBoost trained set. In one advantageous embodiment, the convolutional neural network is trained jointly to the XGBoost using non-annotated ECG data, to take advantage of the patterns identifiable in a larger ECG dataset so as to increase the performance.

In one embodiment, the processor is also configured to input each segment of the episode into a neural network and extract as output of the neural network at least one neural network feature of the segment. In this embodiment, for each segment the calculated feature of the segment is at least one of the following: rhythm feature, morphological feature and/or neural network features.

Each segment in each episode may be segmented into at least two sub-segments of equal duration. For this step 103, the method uses a sliding window to identify overlapping sub-segments of a fixed duration. For example, each segment may be segmented into 10 second sub-segments that each begin 1 second apart.

The method may further comprise a step 104 of using the R waves identified in said sub-segment for calculating at least one feature of each sub-segment.

Notably, variation features, rhythm features, neural network features and spectral features may be calculated for each sub-segment. The variation features may be the quantiles of the rolling variance of the signal, which may be computed with windows of varying durations. The rhythm features, which may be calculated for each of the four RR interval arrays described above, may include the mean, median, minimum, maximum and standard deviation of the RR interval durations; the mean, median and standard deviation of the absolute variation of the RR interval durations; and the sample entropy of the RR interval durations (using vectors of length 2 and the Chebyshev distance). The spectral features may be the spectral characteristics of the signal based on the Fast Fourier Transform (FFT) of the signal filtered by a bandpass filter. The spectral features may include the fundamental frequency of the signal, the value of the FFT at its fundamental frequency, and the power ratio between the fundamental and its harmonics and the total FFT (calculated with multiple harmonics and frequency width).

Each episode may be analyzed based on its sub-segment features (variation features, rhythm features, neural network features and spectral features) as well as the segment features (morphological features and rhythm features) from which the sub-segment was extracted.

The system and method described herein may be configured to classify each episode as indicative of an asystole, Bradycardia, atrial fibrillation or atrial tachycardia (AT/AF), ventricular tachycardia (VT), an artifact, or a normal heart rhythm. An asystole (or pause) is the absence of any ventricular contraction for a minimum duration, for example the minimum duration corresponding to a configurable Asystole interval). Bradycardia is a slow ventricular rate (for example, a ventricular rate below a configurable Bradycardia rate for a minimum duration of 4 beats). Ventricular Tachycardia may be at least one of the following: a tachycardia that originates in the ventricle, or a non-sustained ventricular tachycardia. An Atrial Tachycardia/Atrial Fibrillation (AT/AF) is at least one of the following: an atrial tachycardia (ectopic), an atrial flutter, or an atrial fibrillation. An artifact is the presence of a non-cardiac noise. In the absence of any of the five aforementioned abnormal heart rhythms, the system classifies the episode as a normal heart rhythm.

According to one embodiment, the method comprises, for each sub-segment, a step 105, of providing as input to a machine learning algorithm the features of the sub-segment and the features of the segment to which belongs the sub-segment, wherein the machine learning algorithm is configured to output a score vector. In one example, the features of each sub-segment and the features of the corresponding segment may be concatenated into a flattened features vector which will be the input of the machine learning algorithm.

The method may comprise a step 106 of obtaining as output a score vector for each of the sub-segment in which have been segmented the segment(s) of the episode.

The machine learning algorithm may be trained on a dataset comprising a plurality of annotated episodes, wherein the dataset comprises episodes representative of abnormal heart rhythms. The annotated episode of the dataset allows for supervised training of the machine learning architecture. The dataset may as well comprise non annotated episodes to be used in other type of training, such as unsupervised or semi-supervised training strategies.

According to one embodiment, the machine learning algorithm comprises a chain of at least two machine learning algorithms.

In a further step 107, the method may use the score vectors obtained for each sub-segment in one episode to classify the episode so as to discriminate true positives episodes from false positives episodes.

In one exemplary embodiment, to classify each episode, the method uses as machine learning algorithm a classifier chain of five machine learning algorithms (e.g., XGBoost algorithms). Each of the five machine learning algorithm identifies whether the segment is indicative of one of the five aforementioned abnormal heart rhythms More specifically, a first XGBoost instance may be trained using a dataset of annotated samples to qualify the samples as indicative of an asystole or not indicative of an asystole; a second XGBoost instance may be trained using a dataset of annotated samples to qualify the samples as indicative of a bradycardia or not indicative of a bradycardia; a third XGBoost instance may be trained using a dataset of annotated samples to qualify the samples as indicative of atrial fibrillation or atrial tachycardia or not indicative of atrial fibrillation or atrial tachycardia; a fourth XGBoost instance may be trained using a dataset of annotated samples to qualify the samples as indicative of ventricular tachycardia or not indicative of ventricular tachycardia; and a fifth XGBoost instance may be trained using a dataset of annotated samples to qualify the samples as indicative of an artifact or not indicative of an artifact.

If none of the five machine learning algorithms identify any of the aforementioned abnormal heart rhythms, in the score vector, the sub-segment is classified as a normal heart rhythm.

Each episode is classified based on the classifications of the sub-segments within the segment(s) of said episode. For example, if an episode includes a sub-segment that has been classified as an artifact and another sub-segment that has been classified as atrial fibrillation or atrial tachycardia, then the episode is classified as an artifact and atrial fibrillation or atrial tachycardia. In this case the episode is a true positive episode, which has to be reviewed by the medical staff. An episode is classified as a normal heart rhythm if all of the sub-segments within that episode are classified as normal heart rhythm. These kinds of events are the cardiac device false positives, which create a surplus of undesired information recorded and transmitted by the cardiac device, since these are normal events, but erroneously labelled as abnormal, and therefore the medical staff don't need to review them. Indeed, no pertinent information on the clinical state of the patient may be obtained by these normal events erroneously labelled.

In one second exemplary embodiment, the machine learning algorithm is a classifier chain of six machine learning algorithms being trained to classify the episode in at least one of the six classes or none of these six classes. For said chain, different decision-tree-based algorithm may be used such as for example: XGBoost, LightGBM, AdaBoost or Random Forest. In one embodiment the machine learning algorithm is a XGBoost which advantageously offers the best compromise between highest achievable performances and time of training required to obtain the parameters reaching these highest achievable performances.

In one example, the classifier chain comprises six XGBoost. Each of the machine learning algorithm of the chain is trained using a dataset of annotated episodes to qualify the episode as at least one of the following classes: indicative of an asystole, bradycardia, atrial fibrillation or atrial tachycardia (AT/AF), ventricular tachycardia or ventricular fibrillation (VT/VF), an artifact, and a normal or not normal heart rhythm. Each of the machine learning algorithm of the chain is trained as a classifier chain, so that the output of each algorithm is part of the inputs of all the subsequent algorithms. This advantageously allows to improve the classification efficiency of the chain. The classification performed by said chain on each sub-segment provides as output a score vector of dimension six. After classification, said score vector may be filled with "1" or "0", the "1" corresponding to the attribution of a specific label by the corresponding machine learning algorithm of the chain while the "0" correspond to the absence of one specific label. The five coefficients associated to the abnormal cardiac rhythms classes (i.e., all classes except to the normal or not normal heart rhythm class) in each score vector obtained for each sub-segment may be then merged at the episode level using a logical OR on each of the score vectors obtained for one episode. The coefficients associated to the class "normal or not normal heart rhythm" in each score vector obtained for each sub-segment may be merged at the episode level with a logical AND. This example provides an episode score vector of six coefficients comprising Booleans, wherein five coefficients (e.g., the first five) are set to "1" whenever at least one of the sub-segment in the episode has been classified in one of the abnormal cardiac rhythms classes and one coefficient (e.g., the last one) is set to "1" if all the sub-segments in the episode have been labelled as "normal heart rhythm". This episode score vector is finally converted into an output configured to qualify the episode as normal heart rhythm, so false positive, or as abnormal heart rhythm, so as true positive. The output, further to the information that the episode is a true positive episode, may as well comprise the label of the at least one abnormal cardiac rhythms classes to which the sub-segment of the episode have been associated.

In one embodiment, the method receives as input episodes from a plurality of cardiac devices from a plurality of manufacturers. Advantageously, the method may comprise a step for normalizing the episodes received from the plurality of cardiac devices, which allows to remove the mean and variance of the input signal so that it is comparable to the others signals.

The platform may be configured to provide functionality for healthcare professionals to view the ECG episodes, the determinations made by the cardiac device, and the determinations made by the method/system of the present invention. If an episode is classified as a normal heart rhythm or artifact, the platform may be configured to refrain from outputting an alert to healthcare professional. By classifying the ECG episodes as described above, the disclosed system reduces the number of false positive alerts that must be reviewed by physicians.

Embodiments disclosed herein include various operations that are described in this specification. As discussed above, the operations may be performed by hardware components and/or may be embodied in machine-executable instructions, which may be used to cause a general-purpose or special-purpose processor programmed with the instructions to perform the operations. Alternatively, the operations may be performed by a combination of hardware, software, and/or firmware.

The performance of one or more operations described herein may be distributed among one or more processors, not only residing within a single machine, but deployed across a number of machines. In some examples, the one or more processors or processor-implemented modules may be located in a single geographic location (e.g., within a home environment, an office environment, or a server farm). In other embodiments, the one or more processors or processor-implemented modules may be distributed across a number of geographic locations.

The present invention relates as well to a system for analyzing electrocardiographic episodes previously derived from a cardiac device so as to discriminate true positives episodes, comprising abnormal heart rhythms, from false positives episodes, comprising normal heart rhythms, said system comprising at least one processor and all necessary circuitry and/or storage medium to implement the method described here above.

The system may be implemented by server (i.e. remote monitoring platform) receiving data from at least one cardiac devices corresponding to at least one patients. The communication of the data to the remote monitoring platform may be done through a communication network such as the internet.

The present invention further relates to a computer readable storage medium comprising instructions which, when the program is executed by a computer, cause the computer to carry out the steps of the method for analyzing electrocardiographic episodes previously derived from a cardiac connected device described here above.

Computer programs implementing the method of the present embodiments can commonly be distributed to users on a distribution computer-readable storage medium such as, but not limited to, an SD card, an external storage device, a microchip, a flash memory device, a portable hard drive and software websites. From the distribution medium, the computer programs can be copied to a hard disk or a similar intermediate storage medium. The computer programs can be run by loading the computer instructions either from their distribution medium or their intermediate storage medium into the execution memory of the computer, configuring the computer to act in accordance with the method of this invention. All these operations are well-known to those skilled in the art of computer systems.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

The present invention further relates to a computer program product for analyzing electrocardiographic episodes previously derived from a cardiac connected device, the computer program product comprising instructions which, when the program is executed by a computer, cause the computer to carry out the steps of the method according to any one of the embodiments described hereabove.

The computer program product to perform the method as described above may be written as computer programs, code segments, instructions or any combination thereof, for individually or collectively instructing or configuring the processor or computer to operate as a machine or special-purpose computer to perform the operations performed by hardware components. In one example, the computer program product includes machine code that is directly executed by a processor or a computer, such as machine code produced by a compiler. In another example, the computer program product includes higher-level code that is executed by a processor or a computer using an interpreter. Programmers of ordinary skill in the art can readily write the instructions or software based on the block diagrams and the flow charts illustrated in the drawings and the corresponding descriptions in the specification, which disclose algorithms for performing the operations of the method as described above.

The invention claimed is:

1. A computer-implemented method for analyzing electrocardiographic episodes previously derived from a cardiac connected device so as to help to discriminate true positives episodes, comprising abnormal heart rhythms, from false positives episodes, comprising normal heart rhythms, said method comprising:
   receiving the episodes, each episode comprising at least one segment of electrocardiographic signal;
   for each segment in one episode:
      identifying R waves in the segment using at least one algorithm and using said R waves for calculating at least one feature of the segment;
      segmenting the segment into at least two sub-segments;
      for each sub-segment:
         using the R waves being comprised in said sub-segment for calculating at least one feature of the sub-segment;
         providing as input to a machine learning algorithm the at least one feature of the sub-segment and the at least one feature of the segment and obtaining as output a score vector, the machine learning algorithm being configured to output said score vector;
   using the score vectors obtained for each sub-segment in one episode to classify the episode so as to discriminate true positives episodes from false positives episodes; and
   outputting the classification results, comprising at least the true positives episodes.

2. The method of claim 1, further comprising providing the true positive episodes to a remote monitoring platform.

3. The method of claim 1, wherein for each segment in one episode the calculated at least one feature of the segment is at least one of the following: morphological feature and/or rhythm feature.

4. The method of claim 1, wherein for each sub-segment the calculated feature of the sub-segment is at least one of the following: rhythm feature, variation feature and/or spectral feature.

5. A system for analyzing electrocardiographic episodes previously derived from a cardiac device so as to discriminate true positives episodes, comprising abnormal heart rhythms, from false positives episodes, comprising normal heart rhythms, said system comprising:
   at least one input adapted to receive the episodes, each episode comprising at least one segment of electrocardiographic signal;
   at least one processor configured to:
   for each segment in one episode:
      identifying R waves in the segment using at least one algorithm and using said R waves for calculating at least one feature of the segment;
      segmenting the segment into at least two sub-segments;
      for each sub-segment:
         using the R waves being comprised in the sub-segment for calculating at least one feature of the sub-segment;
         providing as input to a machine learning algorithm the at least one feature of the sub-segment and the at least one feature of the segment, wherein the machine learning algorithm is configured to output a score vector;

using the score vectors obtained for each sub-segment in one episode to classify the episode so as to discriminate true positives episodes from false positives episodes; and at least one output adapted to provide the true positives episodes.

6. The system of claim 5, wherein for each segment in one episode the at least one feature of the segment is at least one of the following: morphological feature and/or rhythm feature.

7. The system according to claim 6, wherein the morphological features are statistics calculated based on the shape of the ECG signal and the rhythm features are statistics calculated based on time periods between R waves.

8. The system according to claim 6, wherein for each sub-segment the calculated feature of the sub-segment is at least one of the following: rhythm feature, variation feature and/or spectral feature, and wherein the R waves in the episodes are identified using at least two algorithms and the at least one rhythm feature of the segment and/or sub-segment is calculated using the R waves obtained from each of the at least two algorithms.

9. The system of claim 5, wherein the processor is configured for segmenting the segment into at least two overlapping sub-segments.

10. The system of claim 5, wherein for each sub-segment the calculated feature of the sub-segment is at least one of the following: rhythm feature, variation feature and/or spectral feature.

11. The system according to claim 10, wherein the processor is further configured to input each sub-segment of the episode into a neural network and extract as output of the neural network at least one neural network feature.

12. The system according to claim 11, wherein the neural network is a convolutional neural network.

13. The system according to claim 5, wherein the at least one algorithm for identifying R waves is selected from the following list: XQRS detection algorithm, a stationary wavelet transform process and/or an optimized knowledge based (OKB) detection algorithm.

14. The system according to claim 5, wherein the processor further is configured to identifying R waves in the segment using at least two algorithms and to use a combining algorithm configured to combine the R waves obtained from said at least two algorithms.

15. The system according to claim 5, wherein the machine learning algorithm is an XGBoost algorithm.

16. The system according to claim 5, wherein the machine learning algorithm is trained on a dataset comprising a plurality of annotated episodes, wherein the dataset comprises episodes representative of abnormal heart rhythms.

17. The system according to claim 16, wherein the dataset of annotated episodes comprises episodes associated to an asystole, bradycardia, atrial fibrillation, atrial tachycardia, ventricular tachycardia and/or an artifact.

18. The system according to claim 5, wherein the input is further configured to receive episodes from a plurality of cardiac devices from a plurality of manufacturers.

19. The system according to claim 18, wherein the processor is further configured to normalize the episodes received from the plurality of cardiac devices.

20. A non-transitory computer readable storage medium comprising instructions which, when the program is executed by a computer, cause the computer to carry out the method according to claim 1.

* * * * *